United States Patent [19]

Winchell et al.

[11] Patent Number: 4,904,239
[45] Date of Patent: Feb. 27, 1990

[54] INFUSOR HAVING A DISTAL FLOW REGULATOR

[75] Inventors: David A. Winchell, Spring Grove; Derek Walsh, Fox Lake, both of Ill.

[73] Assignee: Baxter International Inc., Deerfield, Ill.

[21] Appl. No.: 189,095

[22] Filed: May 2, 1988

Related U.S. Application Data

[60] Division of Ser. No. 51,174, May 14, 1987, Pat. No. 4,741,733, which is a continuation of Ser. No. 689,420, Jan. 7, 1985, abandoned.

[51] Int. Cl.⁴ ............................................. A61M 5/00
[52] U.S. Cl. ..................................... 604/51; 604/132; 128/DIG. 12
[58] Field of Search ................. 604/51, 132, 249, 251, 604/257, 296; 222/107, 215, 386.5; 128/DIG. 12

[56] References Cited

U.S. PATENT DOCUMENTS

| | | | |
|---|---|---|---|
| 3,675,891 | 7/1972 | Reynolds et al. | 604/249 |
| 3,895,631 | 7/1975 | Buckles et al. | 604/132 |
| 3,985,336 | 10/1976 | Bentley | 604/249 |
| 4,201,207 | 5/1980 | Buckles et al. | 604/132 |
| 4,202,333 | 5/1980 | Thill et al. | 604/135 |
| 4,337,769 | 7/1982 | Olson | 128/DIG. 12 |
| 4,381,006 | 4/1983 | Genese | 128/DIG. 12 |
| 4,414,999 | 11/1983 | Basta | 604/249 |
| 4,419,096 | 12/1983 | Leeper et al. | 604/132 |
| 4,497,468 | 2/1985 | Hubbard et al. | 604/249 |

FOREIGN PATENT DOCUMENTS 8204399 12/1982 PCT Int'l Appl. .

OTHER PUBLICATIONS

*Introduction to Fluid Mechanics*, Fox and McDonald, 2nd Ed., John Wiley & Sons ©1973, 1978.

Primary Examiner—Stephen C. Pellegrino
Attorney, Agent, or Firm—Paul E. Schaafsma; Bradford R. L. Price; Paul C. Flattery

[57] ABSTRACT

An infusor (10) is disclosed for dispensing a liquid under pressure at a predetermined flow rate. The infusor (10) includes a housing (12) containing an elastomeric bladder (16) for receiving the liquid under pressure. The liquid is delivered from the bladder to a patient through tubing (36). A non-adjustable, preselected flow regulator (38) includes a capillary bore (48). The flow regulator (38) is disposed at the distal end of the tubing (36), such that the tubing may be primed quickly, in a time period virtually unaffected by the flow regulator (38). Distal placement of the flow regulator (38) results in a more constant temperature, and thus a more constant flow rate, of fluid flowing through the flow regulator.

1 Claim, 1 Drawing Sheet

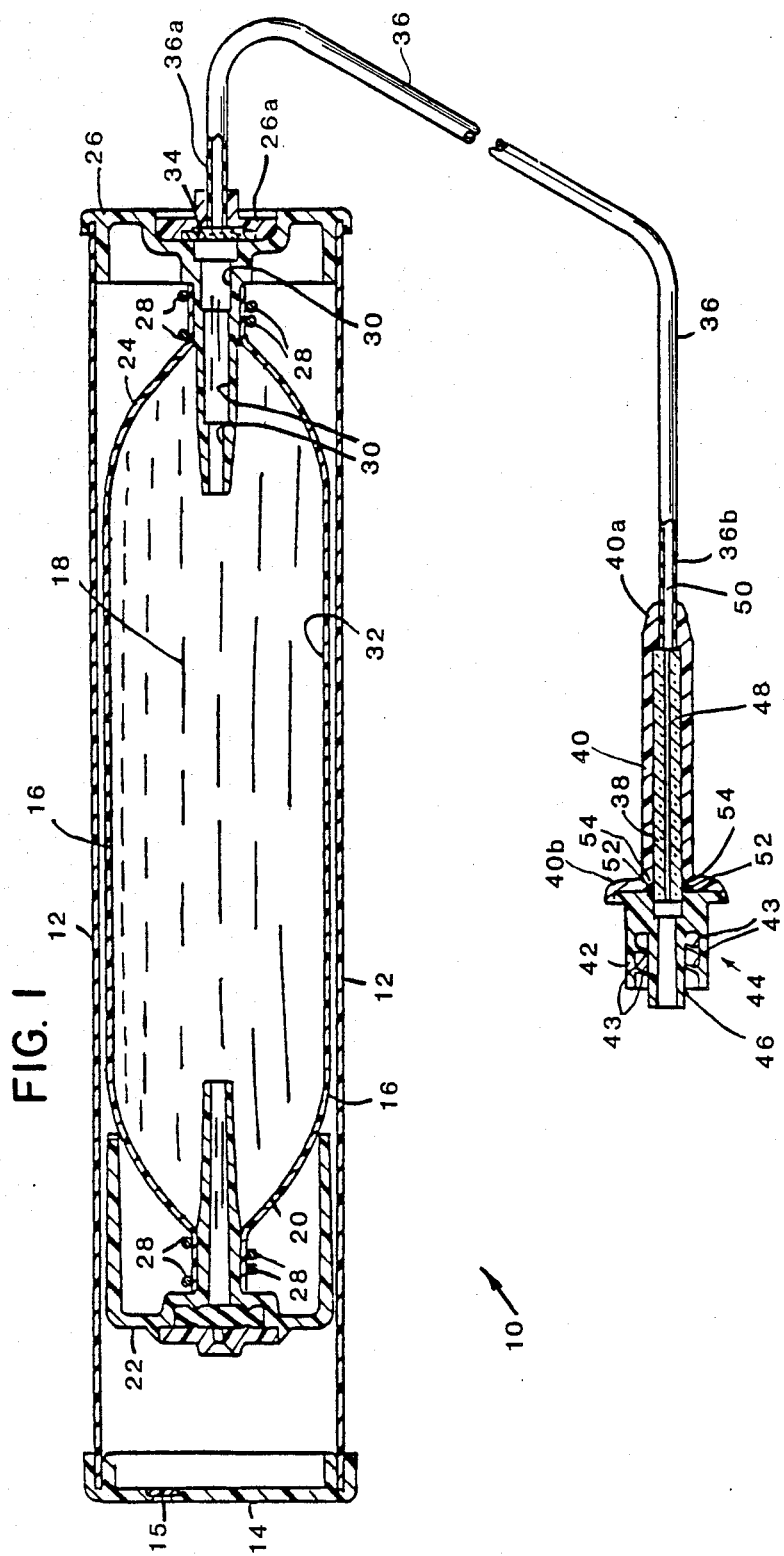
FIG. I

INFUSOR HAVING A DISTAL FLOW REGULATOR

This is a division of application Ser. No. 51,174 filed May 14, 1987, now U.S. Pat. No. 4,741,733, which is a continuation of application Ser. No. 689,420, filed Jan. 7, 1985, now abandoned.

U.S. Pat. No. 4,318,400 to Peery et al. entitled, "Medical Infusor" is incorporated by reference herein.

TECHNICAL FIELD OF THE INVENTION

The present invention relates to an infusor for dispensing drugs in liquid form to a patient.

BACKGROUND OF THE INVENTION

U.S. Pat. No. 4,318,400 referred to above and U.S. Pat. No. 4,386,929 to Peery et al. entitled, "Elastomeric Bladder Assembly" disclose an infusor, a device for delivering a predetermined quantity of a drug or other medicament to a patient in a pre-selected time period at a substantially constant fluid flow rate. The infusor includes a bladder which contains the liquid to be infused. The bladder is pressurized by the liquid to be infused into the patient. Such an infusor is sold by Travenol Laboratories of Deerfield, Ill., Product Code No. 2C1070. That infusor is intended for delivery of medical substances to human patients.

As disclosed in U.S. Pat. No. 4,318,400, the infusor includes a housing, a plug fixed in one end of the housing and having an aperture that extends through the plug, and a tubular elastomeric bladder in the housing for receiving the liquid under pressure. One end of the bladder is sealingly attached to the plug, with the lumen of the bladder communicating with the aperture of the plug. The disclosed infusor further includes a conduit connected to the plug aperture, the conduit and the aperture together defining a dispensing passageway for transporting the liquid from the bladder to the infusion site of the patient. A flow regulator is disposed somewhere in the dispensing passageway for permitting the liquid to flow from the bladder, through the dispensing passageway at a predetermined rate. The flow restrictor comprises a capillary element which is illustrated within the housing.

The infusor is designed to deliver the liquid medicament at a predetermined flow rate. However, with the principal flow restrictor comprising a capillary element, the extent to which the restrictor limits the maximum fluid flow rate out of the infusor is determined by the length and cross-sectional area of the capillary element itself.

If the capillary element is to be maintained within the housing, it becomes difficult to substantially lengthen the capillary element without requiring a re-design of the housing. To avoid such a re-design, the internal diameter of the capillary element may be varied; however, with the small internal diameters utilized in the flow restrictor, such as a capillary of about 0.0016 inch in diameter, it becomes difficult to consistently manufacture capillary elements having the required precise internal diameter. It should be noted that variances in diameter can average out over the length of the capillary element but as noted above, the length of the element is limited when it is disposed within the housing, thereby limiting the extent to which the effect of variances along the length of the capillary element can be minimized. The length of the capillary and flow restrictor in Product Code No. 2C1070 is about 0.316 inch.

Furthermore, although the infusor sold under Product Code No. 2C1070 is designed to deliver a relatively small volume of fluid over a relatively long period of time, such as about 48 ml in twenty-four hours, even slower flow rates are desirable in certain circumstances. As an example only it is sometimes desirable to deliver 36 ml, 48 ml or 60 ml of a medical liquid in three, four or five days, respectively.

With such extremely low flow rates, flow of fluid in the conduit downstream of the flow restrictor is extremely slow, even with a small tubing lumen. Thus, the time required to prime the infusor, i.e., the time to purge the aperture and conduit of air by filling same with liquid, is about fifteen to twenty minutes for example with the infusor sold under Product Code No. 2C1070.

With longer flow restrictors required for slower flow rates the priming time will grow considerably. For example, to delivery the same volume of liquid in four days instead of one day, the flow restrictor will be about 4 times longer, with the same capillary diameter. This would make the priming time about 4 times greater, to about 60 to 80 minutes. It would be desirable to provide an infusor having slower flow rates without increasing the infusor priming time.

The infusor sold under Product Code No. 2C1070 includes O-rings at both ends of the flow restrictor to prevent fluid flow between the housing for the flow restrictor and the outside of the flow restrictor. Because the flow restrictor is between two other elements in the housing the restrictor needs to be sealed with O-rings at both ends. While providing a highly effective seal, it would be desirable to reduce the number of required sealing elements, or O-rings. Also, because the O-rings are disposed at the ends of the flow restrictor, any housing re-design, referred to above regarding a longer capillary element, would necessarily require re-designing the placement of the O-rings in the housing.

It has also been found that the temperature of the liquid to be delivered to the patient by the infusor has a significant effect on the fluid flow rate. This is because the temperature of the liquid affects its viscosity. It would be desirable to provide for a constant liquid temperature in order to provide a constant flow rate. It would also be desirable to know the temperature of the liquid during design of the infusor so that the preselected fluid flow rate could be more easily achieved.

SUMMARY OF THE INVENTION

The present invention provides an infusor which enables quick priming. The present invention makes possible infusors that extend the delivery time of the liquid to longer periods of three to five days for example, requiring an even more restrictive flow restrictor, yet the infusor permits priming in about five minutes. This is so even though the flow regulator in one preferred embodiment is more than four times the length of the flow restrictor used in the above identified Product Code No. 2C1070 infusor. The infusor of the invention prevents a much greater priming time which would otherwise be required using the previously known design.

The infusor of the present invention, when used to deliver about the same amount of fluid in about the same time period as earlier known Product Code No. 2C1070, permits priming of the infusor in even less than five minutes, greatly reducing the priming time as compared with the known priming time of fifteen to twenty minutes.

The infusor of the invention includes a bladder and a housing containing the bladder. A plug is mounted to the housing and includes an aperture extending therethrough. The inside of the bladder is in fluid communication with the aperture in the plug. Tubing is secured at its proximal end to the aperture for transporting the liquid from the bladder to the infusion site of a patient.

A non-adjustable, pre-selected flow regulator is secured adjacent the distal end of the tubing and includes a bore in fluid communication with the tubing lumen. The flow regulator places a maximum limit on the rate of fluid flow out of the infusor.

The flow regulator bore has a cross-sectional area less than that of the tubing lumen so that, with a given cross-sectional bore area, the length of the bore affects the maximum fluid flow rate. Connecting means is secured adjacent the downstream end of the flow regulator for securing the infusor through a separate assembly such as a catheter assembly at the infusion site of a patient.

By requiring the flow regulator to be disposed adjacent the distal end of the tubing and immediately adjacent the connecting means, the infusor of the present invention permits extremely quick priming of the tubing up to the flow regulator, not withstanding the designed low fluid flow rate out of the infusor. With the previously known infusor design all liquid filling the tubing during priming must first pass through the flow restrictor, whereas with the infusor of the present invention liquid filling the tubing during priming can not first flow through the flow regulator; instead, liquid entering the tubing during priming simply forces air out through the regulator, which is the cause of little resistance to liquid priming of the tubing.

The flow regulator of the present invention includes a single uniquely designed seal to block fluid flow around the outside of the flow regulator. The seal includes a sealing element such as an O-ring pressed within and conforming to the shape of an annular channel having a triangular cross-sectional configuration.

The infusor of the present invention recognizes that the effect of liquid temperature, and therefore liquid viscosity, on the fluid flow rate is greatest through the flow regulator. The infusor of the present invention permits the flow regulator to be placed adjacent a patient's skin. By so doing, the patient's body heat stabilizes the temperature of liquid through the flow regulator.

BRIEF DESCRIPTION OF THE DRAWING

The FIGURE illustrates the infusor of the invention, in section including the tubing distal end, flow regulator and connecting means.

DETAILED DESCRIPTION OF THE PREFERRED EMBODIMENT

Referring to the drawing, there is disclosed the infusor 10 of the invention. The infusor 10 includes a tubular housing 12 and an end cap 14 closing one end of the housing 12. An elastomeric bladder 16 contains the liquid drug or other medicament 18 to be infused.

The end cap 14 includes a vent opening covered with a hydrophobic membrane 15. The vent opening ensures that the housing interior stays at atmospheric pressure, even as the bladder expands during filling and contracts during infusion of the liquid contained therein. The hydrophobic membrane 15 keeps the liquid within the housing in the unlikely event that the bladder should leak. This is especially important with some chemotherapy drugs for example, which may be toxic.

The bladder is secured at a free end 20 to a floating piston 22. The bladder 16 is secured at its fixed end 24 to a plug 26 which is mounted to the housing 12. The plug 26 may be made unitary with the housing. The free and fixed ends 20, 24 may be secured to the floating piston 22 and plug 26 respectively by means of wire clamps 28 for example. As liquid is expressed from the expanded bladder 16, the floating piston 22 moves toward the plug 26. The plug 26 includes an aperture 30 extending therethrough which is in fluid communication with the inside 32 of the bladder 16.

A filter element 34 such as a sintered metal filter is mounted across the aperture 30 to filter fluid flowing out of the bladder 16. The plug 26 may include an end piece 26a secured to the plug 26 by sonic welding for example, for mounting the filter element 34 within the plug 26 and for securing plastic tubing 36 to the plug 26.

The tubing 36 includes a proximal end 36a and a distal end 36b. The tubing proximal end 36a is secured by adhesive or the like to the end piece 26a of the plug 26. Alternatively, the tubing may be sold unconnected to the housing and may include an attachment mechanism such as a locking Luer fitment for example, for attaching the tubing to the housing by a hospital pharmacist or other operator. Examples of tubing which may be attached to a pressurized reservoir are disclosed in U.S. Pat. Nos. 3,468,308, 3,469,578 and 3,486,539.

A flow regulator 38 is secured to the tubing adjacent the tubing distal end 36b. In the preferred embodiment the flow regulator 38 is disposed within a rigid plastic regulator housing 40 which is secured by solvent bonding for example at its upstream end 40a about the outside of the tubing distal end 36b. The regulator housing 40 includes an enlarged downstream end 40b forming an annular flange with and being connected to an internally threaded sleeve 42 of a locking Luer 44. The Luer lock 44 includes a Luer taper element 46. The Luer taper 46 is adapted for insertion into the hub of a catheter assembly at the infusion site of a patient. The internal threads 43 on the sleeve 42 are adapted for engaging flanges on the catheter hub assembly, tightly securing the Luer taper element 46 to the catheter assembly. The Luer lock serves as connecting means for securing the infusor to the separate catheter assembly at the infusion site.

A sealing element 52 such as an O-ring is disposed around the periphery of the flow regulator 38 to prevent fluid from flowing between the outside of the regulator 38 and the regulator housing 40. The sealing element 52 is mounted in an annular channel 54 around the periphery of the flow regulator 38. The channel 54 has a triangular cross-section. The three sides of the channel 54 are formed by the flow regulator 38, a beveled corner of the enlarged end 40b of the housing, and the threaded sleeve 42 of the connecting means.

The sealing element 52 is pressed within and conforms to the shape of the channel 54 as the channel 54 is formed. The channel 54 is formed as the sleeve 42 and the enlarged end 40b are secured together, such as by sonic welding. In the preferred embodiment the sealing element 52 is an O made of silicone rubber having an inner diameter of abut 0.11 inch and an outer diameter of about 0.25 inch with a disk shaped cross-section. The pressure placed on the sealing element 52 by the sleeve 42 and enlarged end 40b deforms the sealing element 52 substantially into the shape of the channel 54, effectively sealing between the flow regulator 38 and the housing. Stated differently the axial load placed on the sealing element 52 creates a radial seal. By creating a radial seal instead of an axial seal, the length of the flow regulator 38 is not critical to making an effective seal. Thus, while the length of the flow regulator 38 is important to flow rate, it is no longer critical in manufacturing a good seal. Still further, the seal design permits the use of dramatically different length regulators for different desired flow rates, while still using the same size housing and connecting means. In other words, the preselected flow rate of the infusor can be changed simply by changing the length of the flow regulator. No changes to the connecting means, the regulator housing 40 or other parts of the infusor are required.

Because the threaded sleeve 42 and housing 40 use molded parts, the size and shape of the channel 54 may be accurately reproduced during manufacture. The triangular shaped channel creates an effective and easily reproducible seal structure. Continuing with the example, while the O-ring inner diameter may be 0.11 inch, the flow regulator 38 outer diameter may be 0.13 inch. This stretching of the O-ring 52 not only aids in effective sealing; it inhibits smaller length regulators 38 from sliding in the housing 40.

The flow regulator 38 places a maximum limit on the flow rate of fluid out of the infusor 10. The flow regulator 38 is non-adjustable and is preselected during manufacture to provide a given maximum fluid flow rate for fluid flowing out of the infusor 10.

In the preferred embodiment the flow regulator 38 is made of glass and defines a very small bore 48 in fluid communication with the tubing lumen 50. The flow regulator bore 48 is much smaller than the tubing lumen 50. For example, the tubing lumen 50 may have a cross-sectional area of about $3.1 \times 10^{-4}$ sq. inch whereas the regulator bore 48 may have an internal diameter of 0.0016 inch, providing a cross-sectional area of $2.01 \times 10^{-6}$ sq. inch for the regulator bore 48.

As discussed above, with capillary type flow restrictors such as the flow regulator 38 the upper limit of fluid flow rate provided by the regulator 38 in combination with the pressurized bladder 16 is determined by the cross-sectional area and length of the regulator bore 48. By providing the flow regulator 38 outside of the housing 12, there is no critical restriction on the length of the regulator 38, such as would otherwise be the case within the housing 12. In the preferred embodiment the flow regulator has a length of about 1.290 inch, enabling delivery of about 36, 48 or 60 ml of liquid in a time period of about 3, 4 and 5 days respectively. The length of the bore 48 is approximately inversely proportional to the fluid flow rate out of the infusor 10. Also, with a longer flow regulator 38, minor variances in internal diameter and cross-section of the bore 48 at certain points along the length of the bore become less critical, since these variations are averaged out along the greater bore length. Such variances would be much more critical with a shorter bore length. In other words, greater manufacturing tolerances for the bore 48 are permitted with longer flow regulators 38.

In addition to enabling the use of longer flow regulators for slower delivery rates, placement of the flow regulator at the distal end of the tubing greatly shortens the priming time. In the example described above the priming time is only about five minutes, even though the liquid flow rate out of the infusor is four times less than in the earlier infusor Product Code No. 2C1070.

The bladder 16, although containing only a small volume of liquid, such as about 50 ml, may be pressurized at a pressure of from about 6.7 to 7.7 psi during fluid flow, for example. Without the flow regulator 48 in the housing, fluid from the bladder 16 would flow through the aperture and tubing almost immediately. However, when a flow regulator is disposed in the housing, the time it takes to prime the tubing, being downstream of the flow regulator, becomes quite lengthy. This is inconvenient for the hospital pharmacist, nurse or patient. The infusor Luer taper 46 must remain exposed, albeit under a laminar air flow hood, for example, until the tubing and connecting means are completely primed. Stated differently, the operator does not connect the taper 46 and connecting means 44 to a catheter assembly until air has been purged from the tubing and connecting means.

However, by providing the flow regulator 48 adjacent the tubing distal end, priming up through the tubing distal end, once initiated, is relatively quick, taking about one minute for tubing about three feet in length. It is believed that the reason priming takes even that long is that the capillary bore 48 provides some resistance to the air being purged from the tubing lumen 50. The operator then need only wait for the short time period to prime the regulator bore 48 and the taper 46, which is a relatively short distance compared to the tubing 36. Continuing with the example, the regulator about 1.290 inch long takes about four minutes to prime, resulting in a total priming time for the infusor of about five minutes.

In addition to providing slower fluid flow rates, more precise manufacturing of flow regulators having the proper flow rate restriction and much lower priming times for any given flow rate, placement of the flow regulator at the distal end of the tubing contributes toward constant fluid flow rate throughout delivery of the liquid, which is especially important with medical liquids. With the flow regulator near the connecting means, the flow regulator 38 can be placed adjacent the patient's skin. The patient's body heat maintains the liquid passing through the capillary bore 48 at a relatively constant temperature, regardless of changes in the ambient air. When the infusion site is near the subclavian vein for example, the temperature is about 9° F. This relatively constant temperature provides a relatively constant liquid viscosity in the flow regulator 38 and thus a more constant fluid flow rate through the bore 48.

Although an illustrative embodiment of the invention has been shown and described, it is understood that various modifications and substitutions may be made by those skilled in the art without departing from the novel spirit and scope of the present invention.

What is claimed is:

1. An infusion device for dispensing a liquid under pressure at a predetermined flow rate comprising in combination:
   (a) an elastomeric bladder for receiving the liquid under pressure;
   (b) a housing containing said bladder and defining an aperture extending therethrough, the inside of said bladder being in fluid communication with said defined aperture;
   (c) tubing having proximal and distal ends, said proximal end secured to said aperture for transporting the liquid from said bladder to an infusion site of a patient;

(d) a non-adjustable flow regulator having a preselected flow rate through a defined bore and including upstream and downstream ends, said flow regulator bore being in fluid communication with the lumen of said tubing, said flow regulator being spaced substantially downstream of said tubing proximal end, and placing a maximum limit on the flow rate of liquid out of said infusion device;

(e) connecting means in fluid communication with said tubing lumen and said flow regulator bore and secured to said infusion device downstream of said tubing and said flow regulator, said connecting means being adapted for securing said infusion device to a separate assembly adjacent to the patient;

(f) wherein upon priming of said infusion device, liquid from said elastomeric bladder flows through said tubing upstream of said flow regulator before flowing through said flow regulator, so that the amount of time required to prime said infusion device is largely proportional to the length of said flow regulator and is relatively unaffected by the length of said tubing upstream of said flow regulator; and (g) further wherein the air in said tubing, upstream of said regulator housing, is expressed from said tubing upstream of said flow regulator before the liquid from said elastomeric bladder flows through said flow regulator.

* * * * *